United States Patent [19]

Buster et al.

[11] Patent Number: 5,100,431
[45] Date of Patent: Mar. 31, 1992

[54] SINGLE STITCH SUTURE NEEDLE AND METHOD

[75] Inventors: John L. Buster, Laguna Niguel, Calif.; Paul H. Ernest, Jackson, Mich.

[73] Assignee: Allergan, Inc., Irvine, Calif.

[21] Appl. No.: 589,046

[22] Filed: Sep. 27, 1990

[51] Int. Cl.⁵ .............................................. A61B 17/00
[52] U.S. Cl. .................................. 606/222; 606/224
[58] Field of Search ....................... 606/223, 222, 224

[56] References Cited

U.S. PATENT DOCUMENTS

| | | | |
|---|---|---|---|
| 1,592,535 | 7/1926 | Morton | 606/223 |
| 1,592,897 | 7/1926 | Morton | 606/223 |
| 1,648,451 | 11/1927 | Fisher | 606/223 |
| 4,957,502 | 9/1990 | Takase | 606/223 |

OTHER PUBLICATIONS

Alcon Surgical "SOLITAIRE The Needle Designed Specifically for Small Incision Closure" (Johnson & Johnson).
Ethicon Product Catalog (Johnson & Johnson).
"Ophthalmic Surgery Products" (Nov. 1, 1989) Ethicon (Johnson & Johnson).
A.C.S. The Alcon Closure System Product Reference Guide.
Surgeon-Plus Tip Sheet "Suture Training Manual".

*Primary Examiner*—Stephen C. Pellegrino
*Assistant Examiner*—Gary Jackson
*Attorney, Agent, or Firm*—Gordon L. Peterson

[57] ABSTRACT

A suture comprising a needle including a substantially straight section terminating at one end in a point and a curved section joined to the other end of the straight section. The straight section and the curved section lie in substantially the same plane. The curved section terminates in a proximal end portion, and a suture is coupled to the proximal end portion of the curved section. This needle can be used in a method for closing an incision in the sclera or cornea with only a single stitch.

34 Claims, 2 Drawing Sheets

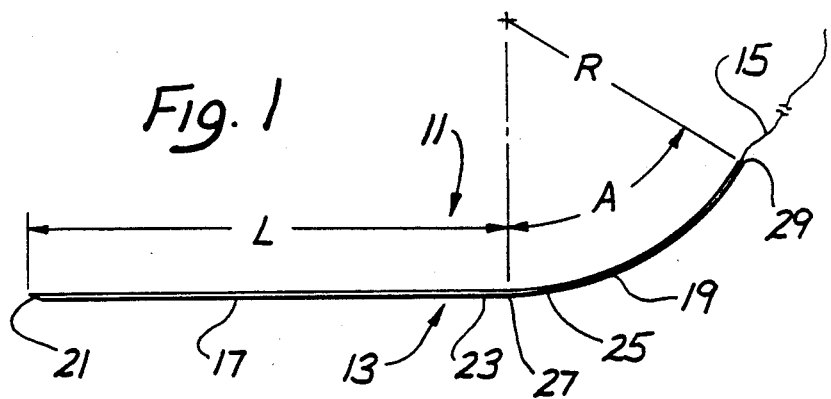
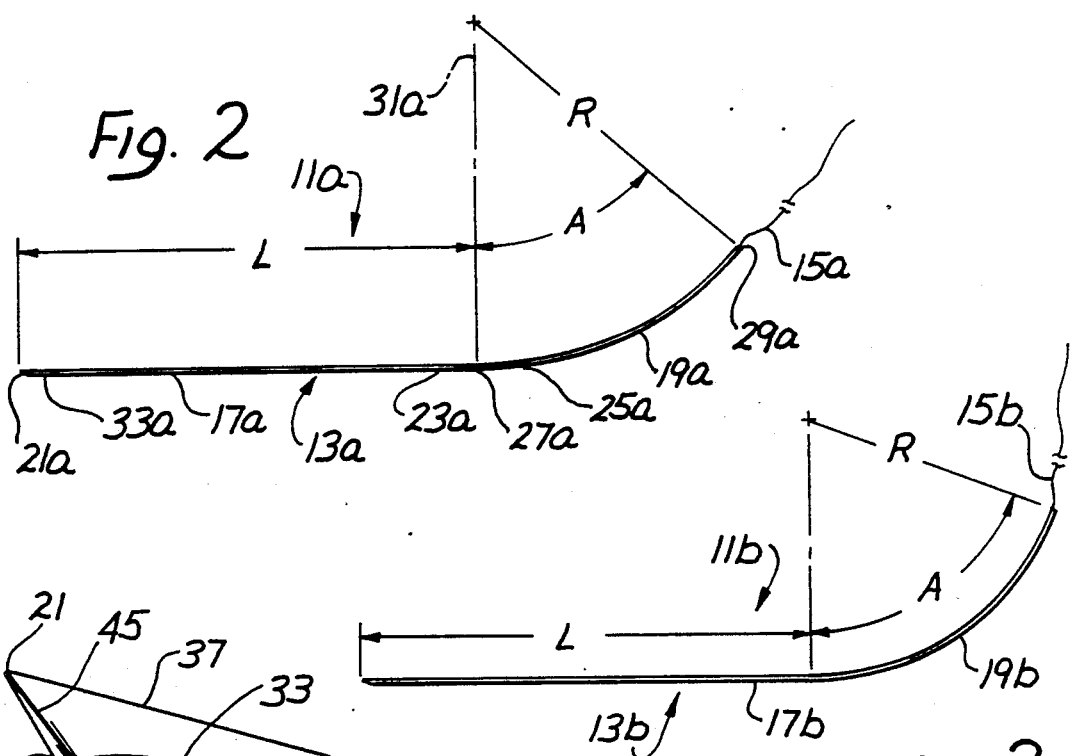
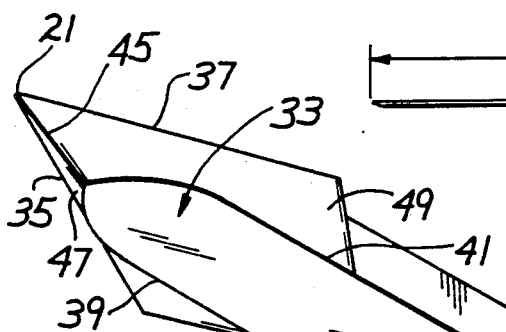
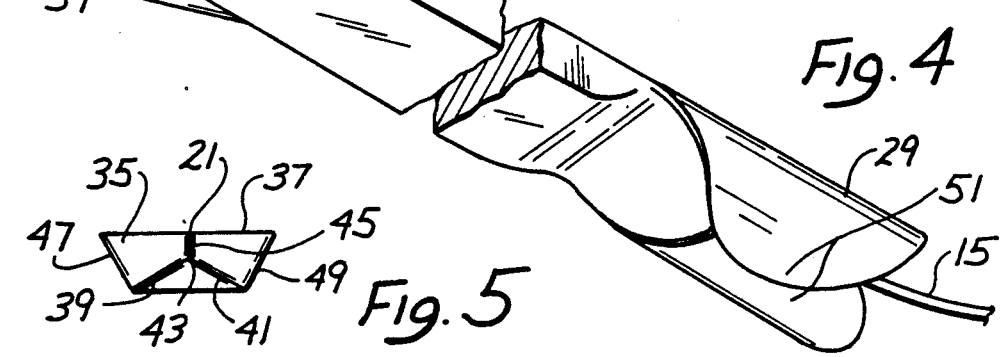

SINGLE STITCH SUTURE NEEDLE AND METHOD

BACKGROUND OF THE INVENTION

Ophthalmic surgery sometimes involves the formation of an ocular incision, for example, in the cornea or sclera. For example, in cataract surgery, an incision is made in the sclera which enables the surgeon to remove the natural lens of the human eye and replace it with an implant known as an intraocular lens. Recent developments in intraocular lens technology have resulted in making the optic of the intraocular lens of soft, flexible material. This enables the intraocular lens to be rolled, folded or otherwise deformed for insertion through the natural lens extraction incision. Consequently, the incision can be of shorter length than is possible for a rigid or non-foldable intraocular lens.

A small ocular incision is very desirable for a number of reasons. For example, a small ocular incision minimizes trauma to the patient, heals more rapidly than a larger incision, and is less subject to infection.

An ocular incision is typically closed with a suture which is commonly considered as comprising a suture needle and a filament attached to the needle. The suture can be used in several different ways to close an ocular incision made in cataract surgery. For example, interrupted stitches can be used, and with this technique, an array of separate stitches are extended transversely across the ocular incision. Alternatively, running stitches which run continuously in zig-zag fashion across the incision may be employed. Finally, a combination of interrupted and running stitches may be utilized to close the ocular incision.

For small ocular incisions of the type used for flexible IOL's, the stitches may take the form of an "X", infinity symbol, or multiple loops through the incision. It has also been proposed to utilize a single stitch running longitudinally of the incision.

One reason that the suturing technique is very important for an incision in the cornea or sclera is that, for some types of stitches, the filament can induce astigmatism. This is the result of the forces exerted by the filament on the cornea or sclera. Prior techniques known to applicants create some likelihood of surgically induced astigmatism.

SUMMARY OF THE INVENTION

This invention provides a suture needle which can be used to close a small incision in the sclera or cornea with a horizontal single stitch. The single stitch is less likely to induce astigmatism. No other suture needle known to applicants can accomplish this closure technique following the same shallow needle track.

In closing a small incision in the sclera or cornea utilizing a horizontal single stitch, it is important that the needle follow a relatively long, shallow track. A shallow "bite" is necessary so that the needle will not extend into the vitreous humor. A relatively long track is necessary so that a single horizontal stitch will be effective in closing the incision. The suture needle of this invention provides the desired long, shallow needle track.

The suture needle of this invention is particularly adapted to close an ocular incision of from about 2.0 mm to about 5 mm in length, with about 3 mm to about 4 mm being optimal. The suture needle provides a relatively long, shallow "bite" of at least 1.8 mm and preferably about 2.5 mm in length and preferably less than 0.5 mm in depth.

The suture needle can advantageously include a proximal section and a substantially straight section. The substantially straight section has a pointed distal end and a proximal region. The substantially straight section enables the suture needle to have the desired long, shallow needle track.

The proximal section has a distal region and a proximal end portion, with at least a portion of the proximal section being curved. The curved nature of the proximal section is useful in developing torque on the suture needle for enabling the suture needle to exit from the tissue at the end of the long, shallow needle track. The distal region of the proximal section is joined to the proximal region of the substantially straight section. The proximal section and the substantially straight section lie substantially in the same plane.

This invention also provides a suture which includes the suture needle and an elongated flexible filament. The filament is coupled to the proximal end portion of the proximal section of the suture needle.

In order to have a bite of the desired length, the length of the substantially straight section is from about 2.3 mm to about 4.5 mm in length. Preferably, the length of the substantially straight section does not exceed about 3.6 mm, and optimally, the length is in the range of from about 3.4 mm to about 3.6 mm.

The substantially straight section should be essentially straight although some very minor and gentle curves may be acceptable. Preferably, the substantially straight section is straight and linear. The proximal section should blend smoothly with the substantially straight section. Although the proximal section may have a linear portion, preferably, it is curved substantially throughout its full length, and optimally it forms a segment of a generally circular arc. The arc, whether circular or not, preferably is between about 10 degrees and about 70 degrees in length, with an arc of about 60 degrees in length being preferred. An arc of less than 10 degrees may not generate sufficient torque for egress of the needle from tissue, and an arc greater than 70 degrees makes it difficult to properly pass the proximal section through tissue.

The total length of the needle as measured along its longitudinal axis or as laid out flat is between about 3.5 mm and about 7.5 mm. The substantially straight section has a distal region with a side-cutting needle configuration which is preferably a reversed ski-shaped configuration. The side-cutting needle is considered desirable for ophthalmic purposes.

The suture of this invention can be used to close an ocular incision with what is referred to in the field of ophthalmology as a single stitch. With this invention, the pointed distal end is inserted into tissue at a first location along one side of the incision. The needle is passed through the tissue along such side of the incision for at least a major portion of the length of the substantially straight section and for a major length of the incision to a second location. The needle is then passed across the incision and through tissue to a third location. From there, the needle is passed, either internally or externally, along the other side of the incision to a fourth location with the filament trailing the needle. Finally, regions of the filament are attached together to close the incision. Of course, the process can begin at any of such locations and be carried out either clockwise or counterclockwise. The major length of the incision through which the needle is passed is at least 1.8 mm and is preferably in the range of from about 2 mm to about 2.5 mm. In passing the needle from the first location to the second location, the needle should not extend into the vitreous humor, and typically, this means that the depth of the needle track should not exceed about 0.5 mm. The curved section is used to assist in exiting the needle from the tissue at the second location. At the fourth location, the needle may again be passed through tissue before the regions of the filament are attached together to close the incision. This method is adapted for closing an incision in the sclera or cornea having a length of about 2.0 mm to about 5 mm and is particularly adapted to close an incision of about 3 mm to about 4 mm.

The invention, together with additional features and advantages thereof, may best be understood by reference to the following description taken in connection with the accompanying illustrative drawing.

BRIEF DESCRIPTION OF THE DRAWING

FIGS. 1-3 are side elevational views of three embodiments of suture needles constructed in accordance with the teachings of this invention.

FIG. 4 is a perspective view illustrating the distal tip construction of each of the three embodiments of suture needles and the filament attachment at the proximal end.

FIG. 5 is an end elevational view of the pointed distal tip and is applicable to all three embodiments.

DESCRIPTION OF THE PREFERRED EMBODIMENT

Figure 6:
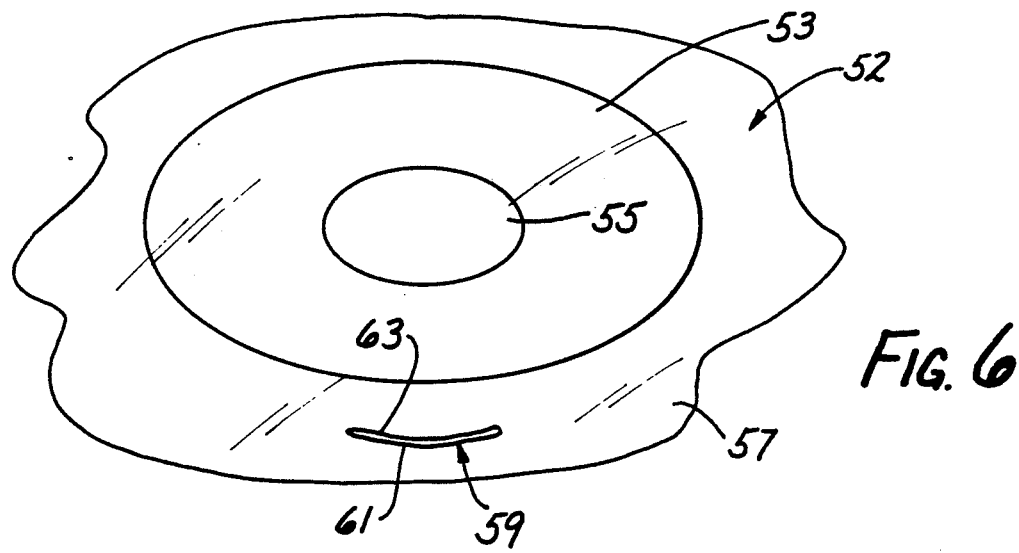
FIG. 6 is an isometric view of a region of the eye.

FIG. 1 shows a suture 11 which comprises a suture needle 13 and an elongated, flexible filament 15. The suture needle 13 is integrally constructed from a single piece of stainless steel wire in the range of 4 to 8 gauge.

The needle 13 includes a substantially straight section 17, which in this embodiment is completely straight, and a proximal section, which in this embodiment is in the form of a curved section 19. The straight section 17 has a pointed distal end 21 and extends proximally to a proximal region 23 where it is integrally joined to a distal region 25 of the curved section 19. More specifically, the straight section 17 terminates at a location 27, and at this location, the curved section 19 begins. The straight section 17 and the curved section 19 lie in the same plane, and the curved section 19 has a proximal end portion 29 at which it is coupled to the filament 15.

The straight section 17 has a length L of 3.6 mm, and the curved section 19 forms a circular arc A which may extend through 10 degrees to 70 degrees and which, in this embodiment, extends through 60 degrees. In the embodiment of FIG. 1, the radius R of the circular arc is 2 mm, and the center of the arc is located on a reference line 31 which is perpendicular to the straight section 17 at the location 27. The overall length of the suture needle 13 as measured along the longitudinal axis of the needle, i.e., the length L plus the length of the arc A, is about 5.69 mm.

The straight section 17 has a side cutting distal tip region 33 which terminates in the pointed distal end 21. This configuration, which is shown in FIGS. 4 and 5, is conventional and comprises cutting edges 35 and 37 which are inclined toward each other as they extend toward the pointed distal end 21 where they terminate. The distal tip region 33 also has converging edges 39 and 41 which converge toward a point 43 which in turn is joined to the pointed distal end 21 by a sharp edge 45. Plain surfaces 47 and 49 are bounded by the edges 35, 39, 45, 37 and 41 as shown in FIGS. 4 and 5.

The filament 15 can be of conventional construction, and as such, may be constructed of any known suitable suture material, such as Nylon, Dacron and silk. The filament may have any suitable length, such as 6 to 9 inches, and may be coupled to the proximal end portion 29 using any suitable technique. For example, the proximal end portion 29 may be provided with integral deformable flaps 51 which can be folded over an end portion of the filament 15 to securely couple the filament to the needle 13. Of course, this is merely illustrative of one form of technique that can be used for this purpose. As shown in FIGS. 1-4, the needle as viewed in side elevation is of substantially constant thickness between the pointed distal end 21 and the deformable flaps 51 which are used to couple the filament 15 to the deformable end portion 29.

FIG. 2 shows a suture 11a which is identical to the suture 11 in all respects not shown or described herein. Portions of the suture 11a corresponding to the suture 11 are designated by corresponding reference numerals followed by the letter "a." The only differences between the suture 11a and the suture 11 are in the dimensions of the suture needle 13a. More specifically, the straight section 17a has a length L of 3.4 mm, and the curved section 19a extends through an arc A of 50 degrees with a radius R of 2.6 mm. The length of the needle 13a measured along the axis of the needle is about 5.67 mm.

FIG. 3 shows a suture 11b which is identical to the suture 11, except for certain dimensions of the suture needle 13b. Portions of the suture 11b corresponding to portions of the suture 11 are designated by corresponding reference numerals followed by the letter "b." The straight section 17b has a length L of 3.4 mm, and the curved section 19b extends through an arc of 70 degrees, with the arc having a radius R of 2.9 mm. The overall length of the needle 13b as measured along the longitudinal axis of the needle is about 5.72 mm. The dimensional data for the sutures 11, 11a and 11b are purely illustrative and do not represent the full range of dimensions or configurations that can be employed with this invention.

Use of the sutures 11, 11a and 11b is illustrated by way of example in FIGS. 6-10. Of course, any of these sutures can be employed in connection with the method of this invention.

FIG. 6 shows the exterior of a human eye 52. The eye 52 includes a cornea 53, a pupil 55 and a sclera 57. An incision 59 has been cut in the sclera 57 below the cornea 53, and through this incision, the natural lens of the eye 52 has been removed and a foldable IOL has been inserted into the posterior chamber (not shown) as a replacement for the natural lens. The incision 59, which may be, for example, about 4 mm in length is closed with a single stitch suture as shown in FIGS. 7-10. The incision 59 has a lower side 61 and an opposite upper side 63. More specifically, the incision 59 forms a tunnel 60 having a floor 62 on the lower side and a flap 64 on the upper side. Of course, the incision 59 can have various different orientations, and the terms "upper" and "lower" have reference to the specific embodiment illustrated.

Figure 7:
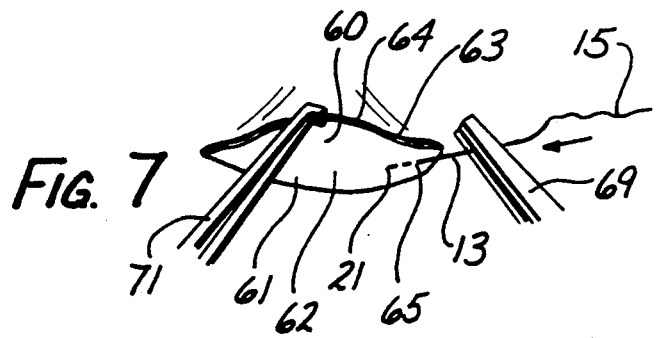
FIGS. 7-10 are isometric views illustrating one way that the single suture method of this invention can be carried out.

The pointed distal end 21 is inserted into tissue at a first location 65 of the floor 62 (FIG. 7) along the lower side 61 of the incision, and the needle 13 is passed through the tissue along a long, shallow needle track which extends through the floor along the lower side 61 of the incision 59 for about 2.5 mm to a second location 67. The 2.5 mm length constitutes a major portion of the 3.6 mm length of the straight section 17 of the needle 13 and also a major length of the 4 mm incision 59. This can be accomplished, for example, by gripping a region of the straight section 17 adjacent the location 27 with forceps 69 as shown in FIG. 7. The needle track does not extend into the vitreous humor and has a depth no greater than about 0.5 mm. During the insertion of the needle 13 as shown in FIG. 7, another forceps 71 may be used to lift the flap 64. The curved section 19 can be gripped with the forceps 69 and used to apply a torque to the needle 13 which is useful in causing the needle to exit at the location 67.

Figure 8:
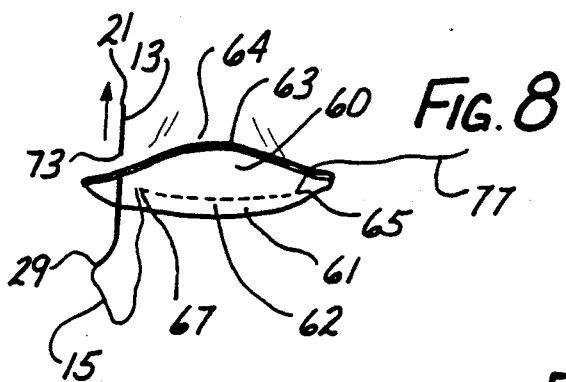
Figure 9:
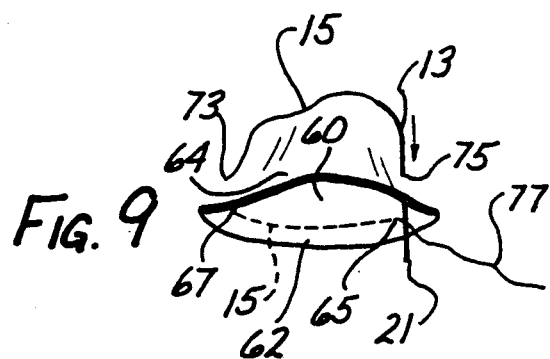
Figure 10:
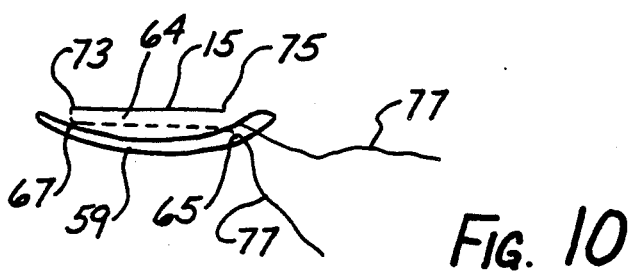

Next the needle 13 is passed across the incision 59 and through tissue of the flap 64 to a third location 73 as shown in FIG. 8. The needle 13 is also passed along the outer surface of the flap 64 and through tissue at a fourth location 75 of the flap, with the filament 15 trailing the needle as shown in FIG. 9. Although the filament 15 may be passed internally through the flap 64 between the locations 73 and 75, the thinness of the flap typically makes this less practical than passing the filament externally over the flap. Finally, the filament 15 is cut to remove the needle 13, and opposite end portions 77 (FIG. 5) may be suitably drawn to the desired degree of tightness and tied or otherwise secured together so as to close the incision 59.

The method described above is exemplary of the way that the suture 11 can be used in a single stitch operation to close the incision 59. However, the sutures 11, 11a and 11b can be used in other ways to close the incision 59. For example, the closure process can begin at the fourth location 75 by extending the needle through tissue at the fourth location to the first location 65 and then from the first location 65 to the second location 67 and so on. Similarly, the suturing technique can be carried out counterclockwise beginning at any of the locations 65, 67, 71 or 73. In any event, regardless of the starting point for the suturing operation, which can be at any of the locations 65, 67, 73 and 75, a single stitch substantially as shown in FIGS. 7-10 is formed with the filament 15 extending along a relatively long, shallow needle track between the locations 65 and 67 and with the filament preferably extending over the outer surface of the sclera 57 between the locations 73 and 75. Although a dual needle suture could also be used, this is not necessary with the present invention because, with only a single horizontal stitch, there is little opportunity for one needle to become dull. Regardless of the location at which the process begins, a primary feature of the method is passing the needle 13 from the first location 65 through tissue along a long, shallow track to the second location 67.

Although an exemplary embodiment of the invention has been shown and described, many changes, modifications and substitutions may be made by one having ordinary skill in the art without necessarily departing from the spirit and scope of this invention.

We claim:

1. A suture comprising:
   a needle including a proximal section and a substantially straight section;
   said substantially straight section having a pointed distal end and a proximal region;
   said proximal section having a distal region and a proximal end portion, at least a portion of the proximal section being curved and such curved portion of the proximal section defining an arc between about 10 degrees and about 70 degrees in length, said distal region of said proximal section being joined to said proximal region of the substantially straight section;
   said proximal section and said substantially straight section lying substantially in the same plane;
   an elongated flexible filament; and
   means for coupling the filament to the proximal end portion of the proximal section.

2. A suture as defined in claim 1 wherein the proximal section is curved substantially throughout its full length.

3. A suture as defined in claim 1 wherein the proximal section forms a segment of a generally circular arc.

4. A suture as defined in claim 1 wherein said substantially straight section is longer than the proximal section.

5. A suture as defined in claim 3 wherein said arc is about 60 degrees in length.

6. A suture as defined in claim 1 wherein the length of the substantially straight section is from about 2.3 mm to about 4.5 mm.

7. A suture as defined in claim 1 wherein the length of the substantially straight section is from about 2.3 mm to about 3.6 mm.

8. A suture as defined in claim 1 wherein the length of the substantially straight section is from about 3.4 mm to about 3.6 mm.

9. A suture as defined in claim 1 wherein the total length of the needle is between about 3.5 mm and about 7.5 mm and the length of the substantially straight section is between about 2.3 mm and 4.5 mm.

10. A suture as defined in claim 1 wherein the substantially straight section is straight.

11. A suture as defined in claim 1 wherein the substantially straight section has a distal region with a side cutting needle configuration.

12. A suture as defined in claim 4 wherein the needle as viewed in said plane is of substantially constant thickness between said pointed distal end and said coupling means.

13. A suture comprising:
   a needle including a curved section and a substantially straight section, said needle having a length between about 3.5 mm and about 7.5 mm;
   said substantially straight section having a pointed distal end and a proximal region, said substantially straight section having a length of from about 2.3 mm to about 4.5 mm;
   said curved section having a distal region and a proximal end portion, substantially all of the curved section being curved, said distal region of said curved section being joined to said proximal region of the substantially straight section;
   said curved section and said substantially straight section lying substantially in the same plane;
   an elongated flexible filament; and
   means for coupling the filament to the proximal end portion of the curved section.

14. A suture as defined in claim 13 wherein the curved section forms an arc of from about 10 degrees to about 70 degrees.

15. A suture as defined in claim 14 wherein the arc is about 60 degrees in length.

16. A suture as defined in claim 13 wherein the length of the substantially straight section is from about 2.3 mm to about 3.6 mm.

17. A suture as defined in claim 13 wherein the length of the substantially straight section is from about 3.4 mm to about 3.6 mm.

18. A suture as defined in claim 13 wherein the substantially straight section has a distal region with a side cutting needle configuration.

19. A method of closing an incision in the sclera wherein the incision has opposite sides, said method comprising:
providing a suture which includes a needle having a substantially straight section with a pointed distal end and a proximal section which includes a curved region and a filament coupled to a proximal region of the proximal section; and
closing the incision in the sclera with the suture.

20. A method as defined in claim 19 wherein the step of closing includes inserting the pointed distal end into tissue at a first location along one side of the incision and passing the needle through the tissue along said one side of the incision, without extending the needle into the vitreous humor, for at least a major portion of the length of the substantially straight section and for a major length of the incision to a second location.

21. A method as defined in claim 20 wherein the substantially straight section has a length of at least 2.3 mm and said step of passing the needle through tissue on one side of the incision is carried out so that said major length of the incision is at least 1.8 mm.

22. A method as defined in claim 20 wherein said step of passing the needle through the tissue along said one side of the incision is carried out without extending the needle deeper than about 0.5 mm.

23. A method as defined in claim 20 including utilizing the curved region to assist in exiting the needle from the tissue at the second location.

24. A method as defined in claim 20 wherein the step of closing includes passing the needle across the incision and through tissue to a third location and internally or externally along the other side of the incision to a fourth location with the filament trailing the needle and attaching regions of the filament together to close the incision.

25. A method as defined in claim 24 including passing the needle through tissue at the fourth location and subsequently carrying out said step of attaching.

26. A method of closing an incision of about 2.0 mm to about 5 mm in the sclera wherein the incision has opposite sides, said method comprising:
providing a suture which includes a needle having a substantially straight section of from about 2.3 mm to about 4.5 mm in length with a pointed distal end and a curved section and a filament coupled to a proximal region of the curved section;
inserting the pointed distal end into tissue at a first location along one side of the incision and passing the needle through the tissue along said one side of the incision at a depth of no greater than about 0.5 mm for at least about 1.8 mm to a second location; passing the needle across the incision and through tissue to a third location, and externally along the other side of the incision to a fourth location with the filament trailing the needle; and
attaching regions of the filament together to close the incision.

27. A method as defined in claim 26 wherein the length of the substantially straight section is at least about 2.5 mm and the step of passing the needle through tissue along one side of the incision is carried out for from about 2 mm to about 2.5 mm to the second location.

28. A method as defined in claim 26 wherein the step of providing includes providing the curved section in the form of a circular arc of from about 10 degrees to about 70 degrees.

29. A method as defined in claim 26 including passing the needle through tissue at the fourth location and subsequently carrying out said step of attaching.

30. A method as defined in claim 26 including utilizing the curved region to assist in exiting the needle from the tissue at the second location.

31. A method of closing an incision in the sclera or cornea wherein the incision provides a tunnel leading to the interior of the eye with the tunnel having a floor and a flap, said method comprising:
providing a suture which includes a needle having a substantially straight section with a pointed distal end and a proximal section which includes a curved region and a filament coupled to a proximal region of the proximal section;
closing the incision using the suture; and
said step of closing includes inserting the pointed distal end into tissue at a first location in the floor of the tunnel and passing the needle through the tissue without extending the needle into the vitreous humor for at least a major portion of the length of the substantially straight section and for a major length of the incision to a second location in the floor.

32. A method as defined in claim 31 wherein the step of closing includes passing the needle from the second location through the flap to a third location and over the flap to a fourth location with the filament trailing the needle and attaching regions of the filament together to close the incision.

33. A suture comprising:
a needle including a proximal section and a substantially straight section;
said substantially straight section having a pointed distal end and a proximal region;
said proximal section having a distal region and a proximal end portion, at least a portion of the proximal section being curved, said distal region of said proximal section being joined to said proximal region of the substantially straight section;
said proximal section and said substantially straight section lying substantially in the same plane;
an elongated flexible filament; and
means for coupling the filament to the proximal end portion of the proximal section, said needle as viewed in said plane being of substantially constant thickness between said pointed distal end and said coupling means.

34. A suture as defined in claim 33 wherein the curved portion of the proximal section is of substantially constant curvature.

* * * * *

UNITED STATES PATENT AND TRADEMARK OFFICE
CERTIFICATE OF CORRECTION

PATENT NO. : 5,100,431

DATED : March 31, 1992

INVENTOR(S) : John L. Buster and Paul H. Ernest

It is certified that error appears in the above-identified patent and that said Letters Patent is hereby corrected as shown below:

Title Page:
In the Abstract, line 6, "suture" should be -- filament -- .

Column 4, line 44, please insert -- A -- after "arc".

Signed and Sealed this

Twenty-first Day of December, 1993

*Attest:*

BRUCE LEHMAN

*Attesting Officer*  *Commissioner of Patents and Trademarks*